United States Patent
Robertson

(10) Patent No.: US 7,892,494 B2
(45) Date of Patent: Feb. 22, 2011

(54) MICRO-DROP DETECTION AND DETACHMENT

(75) Inventor: Gordon Robertson, Elkton, MD (US)

(73) Assignee: Archivex LLC, Baltimore, MD (US)

( * ) Notice: Subject to any disclaimer, the term of this patent is extended or adjusted under 35 U.S.C. 154(b) by 558 days.

(21) Appl. No.: 11/737,267

(22) Filed: Apr. 19, 2007

(65) Prior Publication Data

US 2007/0248498 A1      Oct. 25, 2007

Related U.S. Application Data

(60) Provisional application No. 60/793,533, filed on Apr. 19, 2006.

(51) Int. Cl.
  *B01L 3/02* (2006.01)
  *G01N 1/10* (2006.01)
  *G01N 21/00* (2006.01)

(52) U.S. Cl. .......... 422/100; 422/67; 422/68.1; 422/82.05; 436/164; 436/180; 73/863.32; 73/864; 73/864.01

(58) Field of Classification Search .......... 422/100, 422/67, 68.1, 82.05; 73/863.32, 864, 864.01; 436/164, 180
See application file for complete search history.

(56) References Cited

U.S. PATENT DOCUMENTS

| | | | |
|---|---|---|---|
| 4,041,995 A | | 8/1977 | Columbus |
| 5,601,980 A | * | 2/1997 | Gordon et al. .......... 435/6 |
| 5,957,167 A | * | 9/1999 | Feygin .......... 141/31 |
| 6,003,388 A | * | 12/1999 | Oeftering .......... 73/864.01 |
| 6,116,297 A | * | 9/2000 | Feygin .......... 141/31 |
| 6,235,534 B1 | * | 5/2001 | Brookes et al. .......... 436/164 |
| 6,387,330 B1 | | 5/2002 | Bova et al. |
| 6,461,572 B1 | * | 10/2002 | Calfee et al. .......... 422/100 |
| 6,589,791 B1 | | 7/2003 | LaBudde et al. |
| 6,713,021 B1 | | 3/2004 | Shvets et al. |
| 6,869,571 B2 | * | 3/2005 | Ingenhoven et al. .......... 422/100 |
| 7,160,511 B2 | * | 1/2007 | Takahashi et al. .......... 422/100 |
| 7,211,223 B2 | | 5/2007 | Fouillet et al. |
| 2004/0166028 A1 | | 8/2004 | Husar et al. |
| 2006/0133965 A1 | * | 6/2006 | Tajima et al. .......... 422/100 |
| 2008/0047368 A1 | * | 2/2008 | Marziali et al. .......... 73/863 |

OTHER PUBLICATIONS

International Search Report and Written Opinion dated Dec. 21, 2007.

* cited by examiner

*Primary Examiner*—Brian R Gordon
(74) *Attorney, Agent, or Firm*—Laurence A. Greenberg; Werner H. Greenberg; Ralph E. Locher

(57) ABSTRACT

An apparatus for accurately dispensing small volumes of liquid from a cartridge having a substantially cylindrical body and a sliding piston and a dispensing tip, wherein an initial starting state is established by electro-optically sensing the position of the liquid meniscus in the dispensing tip, and by adjusting the motion of the piston according to the output of said sensing means. A means for detaching the liquid drop adhering to the dispensing tip by imparting sufficient acceleration to the dispensing tip that the surface tension bond is overcome which substantially improves the accuracy of dispensing small volumes of liquid from the cartridge.

11 Claims, 7 Drawing Sheets

US 7,892,494 B2

MICRO-DROP DETECTION AND DETACHMENT

CROSS-REFERENCE TO RELATED APPLICATIONS

This application claims priority to provisional application No. 60/793,533, filed Apr. 19, 2006.

FIELD OF THE INVENTION

The present invention relates to a method and device for the storing of liquids and the precision dispensing of microliter quantities of such liquids. More particularly, the invention relates to a device for the precision dispensing of liquids, such as precious biologic fluids, by manual or automated means, which maximizes convenience, efficiency, and reliability, and which minimizes contamination during the management of such liquids.

BACKGROUND OF THE INVENTION

The Human Genome Project and various new technologies linking disease phenotypes with cellular genotypes have ushered in a new era in life science research and personalized medicine. Post-genomic era research promises improved clinical diagnostics, better pharmaceutical products and individualized healthcare. Such research begins with asking a specific molecular question of multiple stored precious biologic solutions containing DNA, cDNA, RNA, protein, or other materials isolated from diseased or normal tissue. Such research and practice often require the precise handling of a large number of samples, preferably in an automated apparatus and contained in specialized containers.

At present, precious DNA and other precious liquid biologic samples used for such studies are typically maintained in aqueous form with solvents such as pure water or Tris-EDTA solutions. Such samples are typically stored in plastic containers such as microcentrifuge tubes or multi-well or multi-tube plates. These solutions are stored at temperatures of 4° C. or –20° C., with a small percentage at –80° C. or lower. Among many drawbacks of the current practice, contamination, evaporation, and lack of convenient inventory control are prominent.

A first problem is contamination. Each time a precious liquid biologic sample is needed, its container is thawed, the cap is opened, and a manually directed pipette is inserted to aspirate and transfer the desired amount of solution to a separate receptacle. Manual pipetting is prone to accidental placement of a contaminated pipette tip into a sample. Similarly, automated pipetting, which is typically done with 96-well or 384-well plates, requires prior removal of either a non-sealing plastic closure or an adhesive film to access the solution, which may be repeated many times for a given sample. While removing the seal, the samples may be aerosolized through vibration of the solution, which increases the risk of cross-contamination. This is especially true, for example in 96-well or 384-well plates, where the point of access for each individual sample is either contiguous or in close proximity to points of access for other individual samples. A single contamination event can lead to costly delay and repetition of experiments if detected, and if undetected can cause misinterpretation of experimental results.

A second problem is evaporation. The primary source of evaporation and concentration change is a lack of robust sealing of most microcentrifuge tubes, which permits the exchange of air saturated with precious liquid vapor and unsaturated air. Consequently, investigators often use samples whose precise concentration is unknown, which increases the rate of failed, invalid, non-reproducible, and/or un-interpretable results. Laboratories requiring greater quality control recheck the concentration of the samples prior to each use, a practice that is time consuming, expensive, and also wastes precious biologic materials.

A third problem is a lack of convenient inventory control. Since no convenient standard method exists to continuously track and maintain records of liquid sample availability, volume, and concentration in real-time, laboratory productivity suffers in numerous ways including: underutilization of samples already obtained by the laboratory but which have been lost in refrigerators or freezers; poor planning or avoidance of demanding experiments because it is too time consuming to determine if necessary samples are available in inventory; and inability to conveniently determine whether a proposed collaboration is feasible.

Any system for long term, contamination-free storage of precious liquids requires a contamination-free means for dispensing aliquots of the liquid. Furthermore, the nature of the experiments conducted using the liquids is such that aliquots ranging in volume from 1 to 20 or more microliters are required, with a dispensing precision of a few percent.

Therefore, a need exists for an apparatus and processes that overcome these limitations presently in the art and provide for the inexpensive storage, tracking, and dispensing of precious biologic solutions. Specifically, a need exists for a robust, reliable, and secure long-term storage and precision dispensing system for precious biologic solutions for use in life science research and molecular medicine.

While the reliable, efficient, contamination-free management of precious liquids is a particular problem in current biological investigations, similar problems exist in any area where precious liquids are managed. Examples of such areas include, but are not limited to, chemical reagent design and delivery, perfume design and manufacture, scent design and manufacture, food additive testing and design, drug design and manufacture, pigment design and manufacture, and others.

In the course of biological assays, investigators often require aliquots as small as 1 microliter to be dispensed. With any practical size of dispensing pipette tip, it is not possible to detach a drop smaller than about 5 µl from the tip unless it is ejected by air pressure from within or outside of the pipette tip, or unless it is transferred to the surface of the receiving container by touching. If the precious liquid is kept contamination-free by being permanently stored in the dispensing device, as opposed to being withdrawn through an inserted pipette; ejection using air pressure from behind the liquid is relatively complex and expensive. A simpler ejection method is desired. Furthermore, contamination control requires that the tip of the storage and dispensing device never comes into close proximity with foreign liquids such as may be in a receiving container, so the touch-means of transferring small drops would not typically be acceptable.

The non-intrusive method of dispensing liquids from such a storage cartridge with a slidable piston, such as an injection syringe, is by mechanically depressing the piston, thereby expelling the liquid through an orifice in the cartridge. A precise volume may be dispensed by accurately controlling the mechanical depression of the piston.

However, there is always some degree of compliance in the construction of the cartridge, piston and piston seal. Therefore, when the piston depression force is relaxed, the liquid is sucked back from the tip of the orifice into the storage chamber to an extent determined by the reduction of piston depression force and the compliance of the design. Furthermore, when first inserting the cartridge into a mechanical depressing device, the contact between the depressing device and the cartridge piston may not be intimate, so an unknown gap between the depressing device and the cartridge piston is introduced.

This suck-back effect and this lack of intimate contact introduce an unknown offset between the amount of mechanical depression of the piston and the volume of liquid expelled. The offset is only a factor in the initial aliquot dispensed; subsequent aliquots have a known starting state providing that the pressure on the piston is not relaxed between aliquots.

In biological investigation it is often necessary to dispense only one microdrop of liquid of known volume from a delivery device. The known starting condition must therefore be established by depressing the piston by a distance sufficient to ensure that the liquid has reached the tip of the orifice. Establishing that the liquid has reached the tip of the orifice is conventionally done, for example in medical injections, by depressing the piston until liquid is discharged from the orifice, wasting the expelled liquid. However, in genomic research the value of precious liquids is often too high and available quantity too small to tolerate such waste, and in addition provision for contamination-free storage and disposal of such waste would be expensive and time-consuming. There is a need in the art to provide methods and devices for precise waste-free liquid dispensing.

BRIEF DESCRIPTION OF THE DRAWINGS

For a better understanding of the nature and objects of the present invention, reference should be made to the following detailed description in conjunction with the accompanying drawings, in which.

DETAILED DESCRIPTION

In view of the foregoing disadvantages of known methods and devices for precision liquid dispensing, it is an object of the present invention to provide an improved system and method for the detection of the liquid meniscus surface at a dispensing tip, and for the detachment of a micro-drop adhering by surface tension to the dispensing tip.

This invention teaches a means for monitoring the position of the liquid meniscus, and for depressing the piston by that accurate distance required to achieve the correct starting position before dispensing. A feature of the invention is a novel means for reliably detaching a small drop of liquid from the dispensing tip of a dispensing device using an inexpensive apparatus external to the storage cartridge provided.

A novel liquid storing and dispensing cartridge permits the storage of precious liquids for long periods with reduced evaporation risk and better-controlled contamination risk, and enables non-intrusive precision aliquot dispensing. Such a cartridge is disclosed in U.S. Patent Application Publication No. 20040256415.

Figure 1:
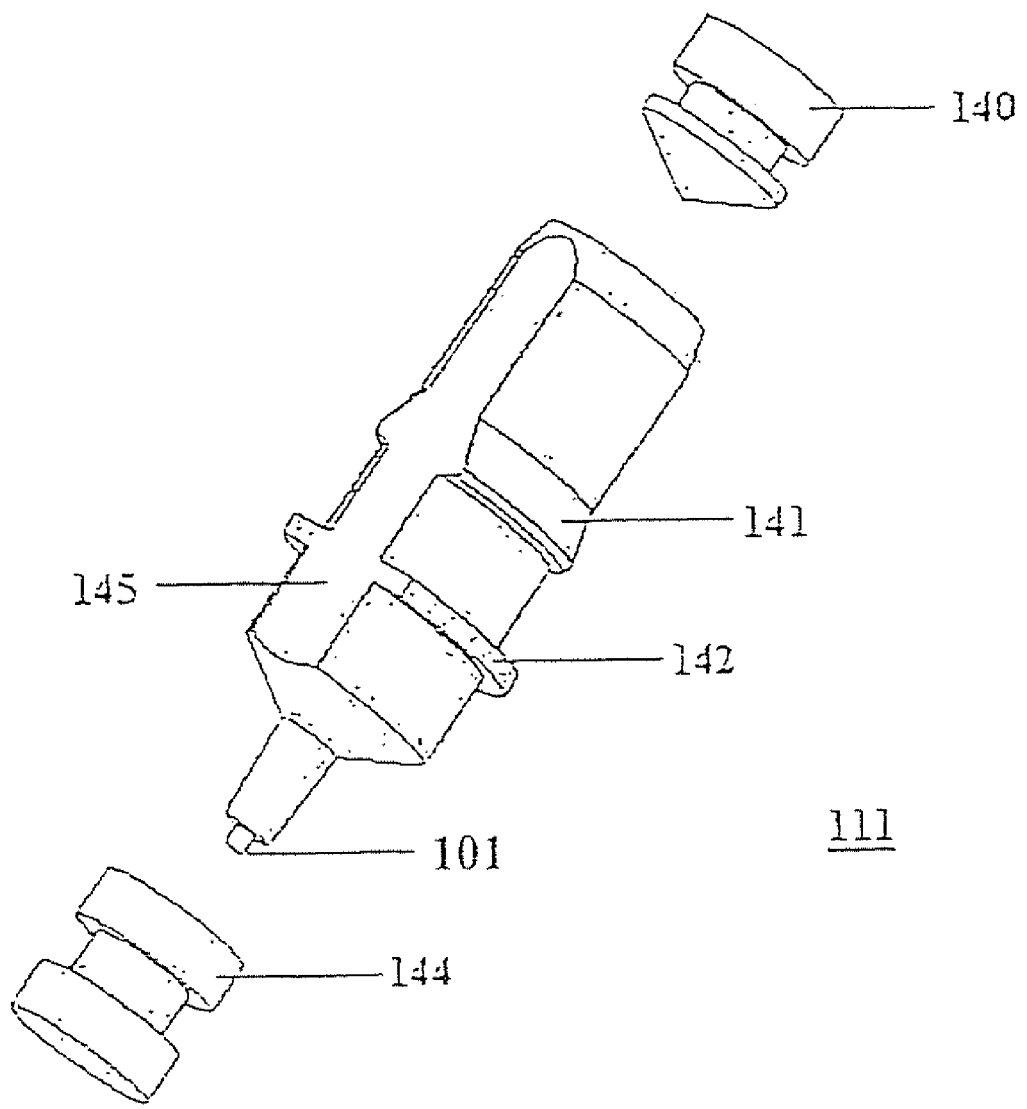
FIG. 1 is a perspective view of a liquid cartridge for storing and dispensing the liquids by the present invention.

One embodiment of a cartridge according to the present invention is given in FIG. 1. The cartridge 111 is a cylinder that can be molded or machined from a variety of materials including metals, plastics and glasses and which typically holds volumes of up to 10 milliliters. It has a piston 140 which seals one end and is used to drive liquid through the dispensing tip 101. A support shoulder 142 and a gripping flange 141 are features in this embodiment used to securely and reversibly attach the cartridge to a piston-moving device. A tip cap 144 is shown which is used for the storage of the liquid containing cartridge. A flat feature 145 is shown in this embodiment to which a label can be applied, or on which an identification marker may be etched.

The liquid cartridges can be stored in associated cartridge racks and rack shelving suitable for room temperature, or refrigerator or freezer temperatures. Each cartridge can be uniquely labeled by human-readable label, barcode label, and/or RFID (Radio Frequency Identification) tag and linked to database systems used for tracking and linking samples to specific experiments and dispensing jobs. Manual and semi-automatic means for filling the liquid cartridges with precious liquids can be carried out with high accuracy and precision. The cartridges are designed to dispense non-intrusively an accurate and precise volume of 0.5 microliters up to the full volume of the cartridge, and to permit the detachment of small drops from the dispensing tip of the liquid cartridge without touching the receptacle or blowing air through the dispensing tip.

To achieve the required dispensing accuracy and precision, the known starting condition must be established by depressing the piston by a distance sufficient to ensure that the liquid has reached the tip of the orifice. In a preferred embodiment, the invention provides a meniscus detection section to detect the emerging meniscus of a microdrop that is made of three components. The first component is a controllable light source such as a diffuse Light Emitting Diode (LED) display with extended surface area, which is used to illuminate the dispensing tip and the emerging meniscus of a nascent drop. The second component is a lens structure used to image the tip of the dispensing tip and the liquid meniscus surface onto the detecting surface of the third component. The third component is a semiconductor image position detecting device, either one-dimensional or two-dimensional, such as a Charge Coupled Device, a Diode Array, a Position Sensitive Device or similar electronic component.

In the preferred embodiment, the position of the light source, the dispensing tip and liquid meniscus, the lens and the image position detecting device are arranged so that any liquid emerging from the dispensing tip causes a change in the apparent position of the end of the dispensing tip, which is detected and used by a controlling device that is described below.

Figure 2:
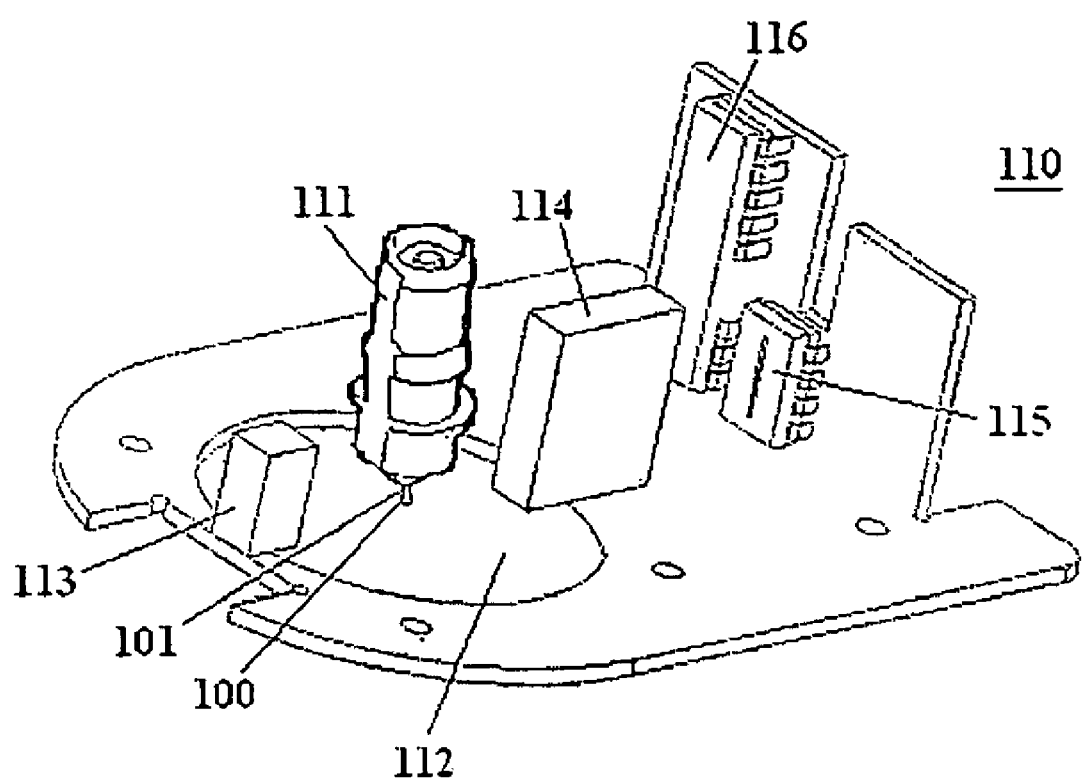
FIG. 2 is a perspective view of one embodiment of the liquid meniscus detection apparatus, with a dispensing tip shown in the appropriate position for detection.

FIG. 2 illustrates a perspective view of a liquid meniscus detection apparatus 110 where a liquid cartridge 111 is positioned such that the dispensing tip 101 and the microdrop 100 are positioned between a diffuse light source 113 and a lens assembly 114 that can focus the image of the microdrop on a semiconductor position detector 115. Although a direct linear optical path from light source 113 to detector 115 is shown and is preferred, the apparatus can include mirrors or other means to permit geometries that do not require alignment of light source 112 to microdrop 100 to lens assembly 114 to detector 115. Other electronic parts 116 may be mounted on the apparatus. These electronic parts 116 can be used to interface the detector 115 with a processor.

Figure 3:
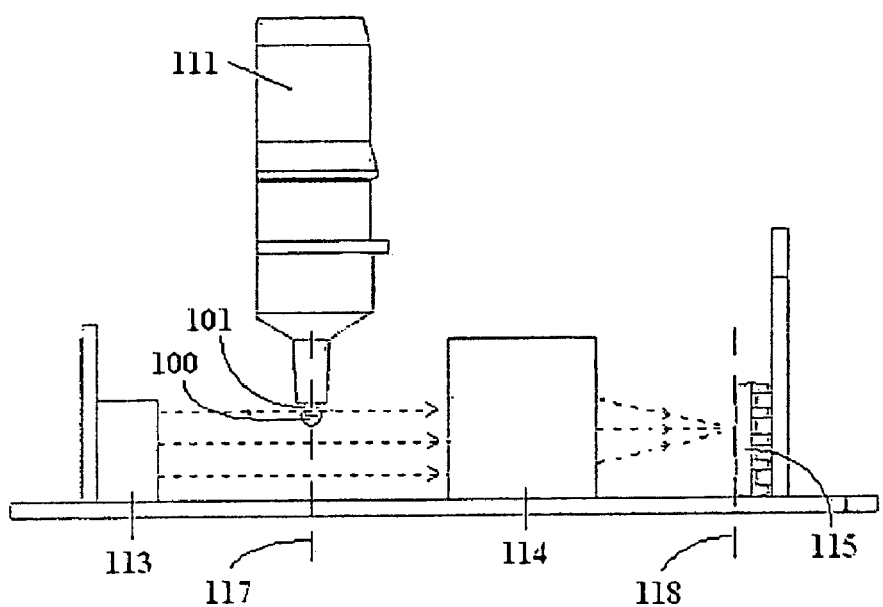
FIG. 3 is a side view of one embodiment of the liquid meniscus detection apparatus, showing the use of a diffuse light source and a lens.

FIG. 3 illustrates a side view of the apparatus of FIG. 2, where in this embodiment a diffuse light source 113 transmits light through the object plane 117 that is defined as perpendicular to the light path and, within which is situated the dispensing tip 101 and microdrop 100 extending downward from the liquid cartridge 111. The light is then focused by the lens assembly 114 to project the image of the microdrop 100 and dispensing tip 101 on the image plane 118 at the surface of the detector 115, which is parallel to the object plane 117. The signal from the detector 115 is then analyzed by a processor to control the dispensing of microdrop of the precious liquid.

Figure 4:
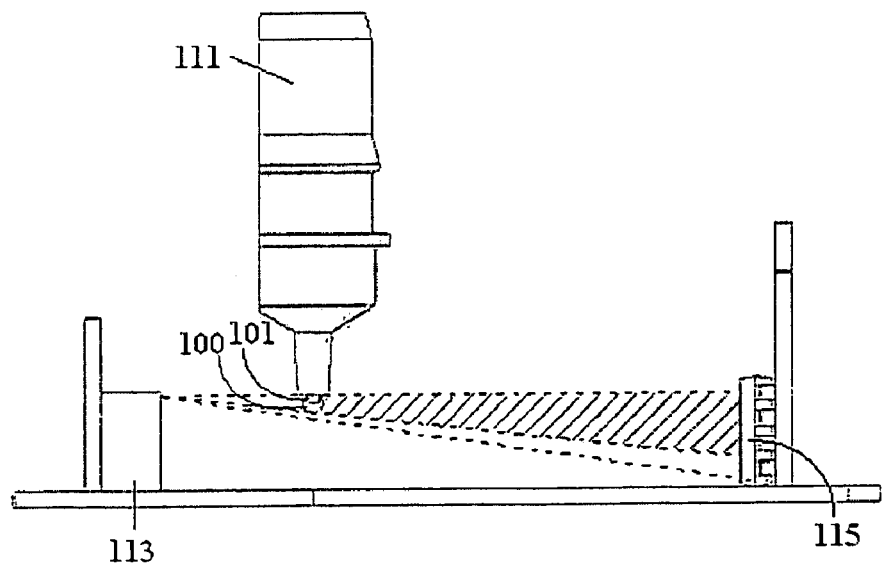
FIG. 4 is a side view of another embodiment of the liquid meniscus detection apparatus, showing the use of a point light source and a cast shadow.

In a second embodiment, the first component is a point light source rather than a diffuse light source, the second component, the lens structure, is omitted so that a sharp shadow of the dispense tip and the liquid meniscus can be cast on the third component, the semiconductor image position detecting device. FIG. 4 illustrates this embodiment, where a point light source 113 transmits light across the dispensing tip 101 and microdrop 100. A shadow is then cast on the surface of the semiconductor position detector 115.

The meniscus detection device described above provides information to a controlling computer. The computer also controls the movement of a mechanical device detachably connected to the piston of the cartridge.

The image position detecting device is connected electronically with suitable control signals and software such that the apparent position of the end of the dispensing tip is transmitted electronically to a computer or controlling device.

In operation, after a cartridge is inserted into the dispensing device, the meniscus detection apparatus registers, and the controlling computer records the apparent position of the dispensing tip. The controlling computer then causes the mechanical device to drive the piston towards the distal end of the cartridge, thus taking up the compliance of the system and ensuring intimate mechanical contact with the piston of the cartridge prior to expelling liquid from the dispensing tip.

As the piston is moved, the meniscus detection apparatus monitors the apparent position of the end of the dispensing tip, until the emergence of the liquid meniscus distorts the light path and causes an apparent change in the position of the dispensing tip. At this instant, the movement of the piston is halted. The controlling computer may calculate the volume of liquid expressed in the meniscus by measuring the apparent position of the dispense tip, and compensate for that volume in the first dispensed aliquot.

Figure 5:
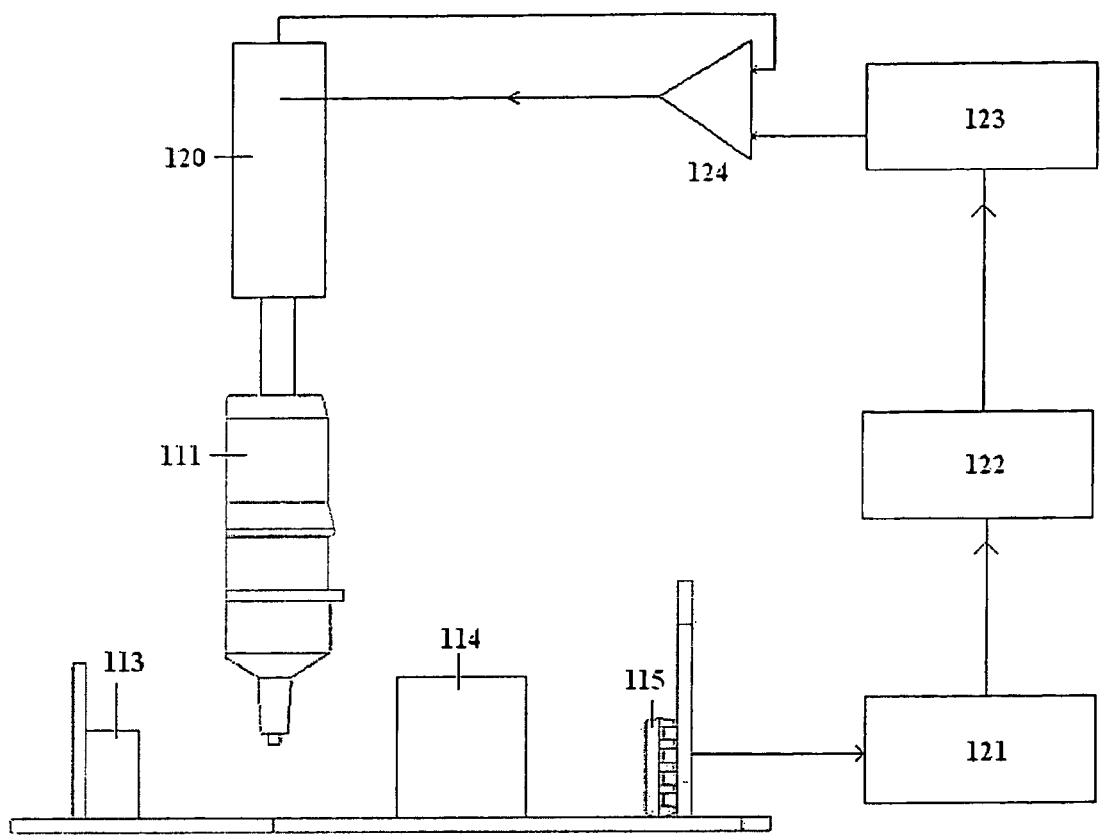
FIG. 5 is a schematic diagram of the control system governing the movement of the mechanical piston-moving device in response to data from the liquid meniscus detection apparatus.

FIG. 5 is a schematic diagram of a dispensing system that includes the detection apparatus and the control system, which governs the movement of a mechanical piston-moving device 120 that moves the piston in the liquid cartridge 111 in response to a drive signal received from a movement control servo device 122. The movement control servo device 122 is controlled by a processor 121 with memory and software to receive a signal from the semiconductor position sensor 115, to analyze the data and to calculate the required piston movement and provide a drive signal to the piston-moving device and receive piston feedback using a movement control servo driver 123. These and other objects have been achieved in the present invention by the critical detecting and controlling of the position of the liquid surface at the dispensing tip before the first aliquot is dispensed, and reliably detaching the micro-drop from the dispense tip after such any aliquot is dispensed resulting in precise aliquot volume control.

Critical to the performance of the invention is a device for the reliable detachment of a microliter sized drop from the dispensing tip of the cartridge. The theory of operation is based on manipulating variables in the surface tension equation that governs the attachment of the drop to the tip of the dispensing device. It is well known by those skilled in the art that the cohesive forces between liquid molecules are responsible for surface tension. The molecules at the surface do not have other like molecules on all sides of them and consequently they cohere more strongly to those directly associated with them on the surface. They will also adhere to molecules at the surface of another body, such as the dispensing tip. Surface tension is measured in dynes/cm, the force in dynes required to break a film of length 1 cm. Water at 20° C. has a surface tension of 72.8 dynes/cm: the surface tension of DNA in a water or Tris-EDTA solution is substantially similar.

Figure 6:
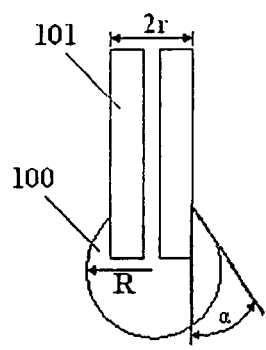
FIG. 6 is a representation of a liquid drop adhering by surface tension to the dispensing tip of the cartridge, and is used to illustrate the terms contained in equations (1) through (6).

When dispensing micro-drops, the interface between the air and the liquid surface occurs at the surface of the dispensing tip. FIG. 6 illustrates the essential features. The vertical adhesion of a drop 100 with surface tension T to the dispensing tip 101 is $$2\pi rT \cos \alpha \tag{1}$$

and the gravitational force on the drop 100 is $$4/3\pi R^3 \rho G \tag{2}$$

where $\rho$ is the density of the liquid. Here the simplifying assumption is made that the drop 100 is spherical.

Simplifying the equation, $$mG = 2\pi rT \cos \alpha \tag{3}$$

where m is the mass of the drop 100.

Adjusting certain of the equation variables may be considered to improve the detachment of the drop 100. The radius of the dispensing tip 101, 'r', can be minimized, but the lowest value is limited by the need to have a capillary tube through the dispensing tip 101. The surface tension 'T' can only be changed by introducing surfactants or other potentially contaminating material into the liquid to be dispensed. The "wetting angle", $\alpha$, may be changed by carefully selecting the material of the pipette, but the range of values is limited. The only other term is the gravitational constant, G.

On the surface of the earth, the gravitational force is not changeable. However, Einstein showed, and it is well understood by those skilled in the art, that a gravitational force and an acceleration field are identical in effect. Changing the acceleration will provide an effect identical to changing G.

To determine the G forces needed to detach a 1 µl drop, m=$10^{-3}$ gram where T is approximately 73, the equation to be solved is:

$$10^{-3} G = 2\pi r . 73 \cos \alpha \quad (4)$$

Assuming a worst case contact angle of zero, the value of cos α=1, so the equation relating the G force needed to detach a drop of water from a dispensing tip of radius r is:

$$G = 448 * 10^3 r \quad (5)$$

The acceleration required to detach a 1 µl drop of water from a dispensing tip of diameter 1 mm is:

$$G = N * 998 = 448 * 10^3 * 0.05 \quad (6)$$

So N=22 Gravities.

As is well understood by those skilled in the art, this calculated value is affected by many poorly controlled variables, so should not be considered particularly accurate. However, it may be agreed that acceleration in the order of 25 standard gravities is sufficient for the detachment of a 1 µl drop.

The invention therefore provides means for imparting an acceleration of more than 25 standard gravities to a liquid cartridge with a dispensing tip to cause any drop of 1 µl or larger to be detached.

In a preferred embodiment, the invention provides a drop detachment device that is compact, inexpensive, reliable and external to the cartridge, thus keeping the complexity of the cartridge as low as possible.

The portion of the invention designed for dispensing the precious liquid and detaching the microdrop is made up of three main components. The first component is a means for detachably grasping the liquid cartridge and the mechanism for moving the piston within that cartridge in a manner which forms a rigid assembly with respect to each component, yet which assembly as a whole may be subjected to a high acceleration.

Figure 7:
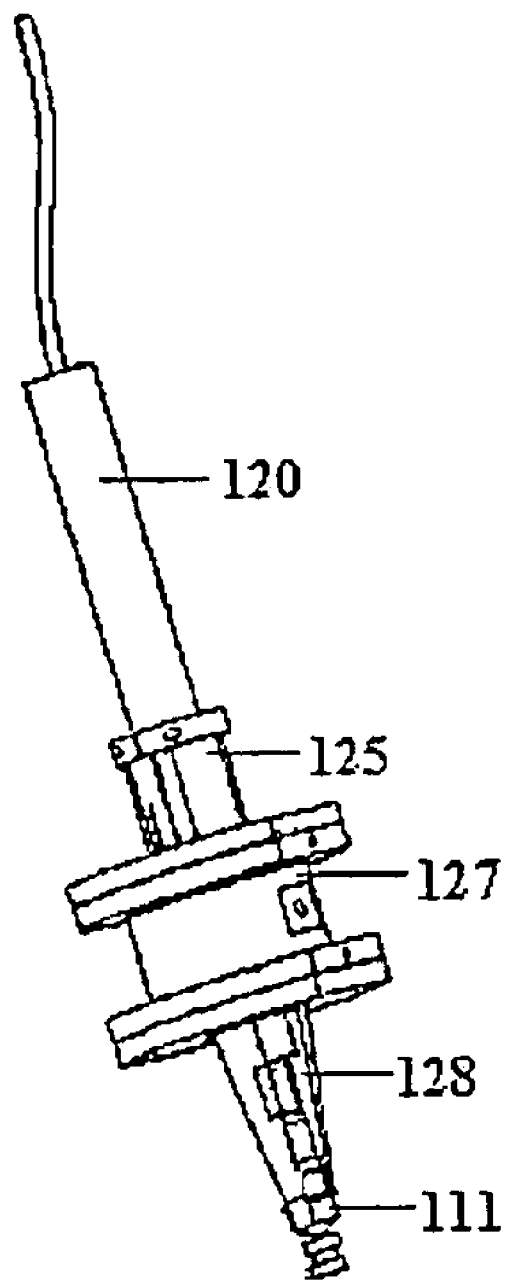
FIG. 7 is a perspective view of one embodiment of the apparatus for removably grasping the liquid cartridge and the mechanical piston-moving device into a rigid assembly.
Figure 8:
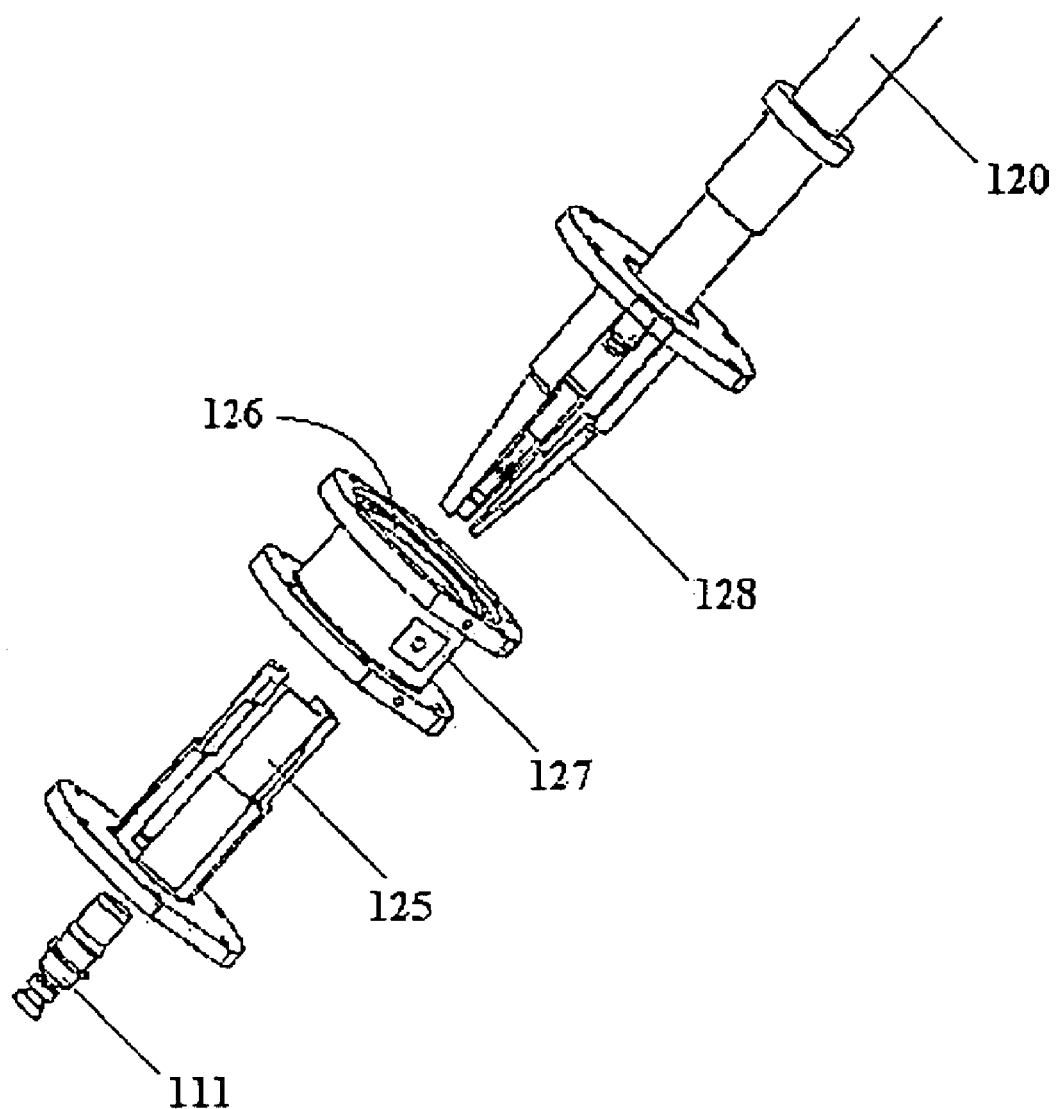
FIG. 8 is an exploded view of one embodiment of the apparatus for removably grasping the liquid cartridge and the mechanical piston-moving device into a rigid assembly.

FIG. 7 is a perspective view of one embodiment of the apparatus for reversibly coupling the mechanical piston-moving device 120 and the liquid cartridge 111 by engaging a cartridge holder 128 via pressurizing a pneumatic bladder contained in a bladder holder 127 to result in a rigid assembly and permitting the removal of the liquid cartridge 111 after depressurizing the bladder. FIG. 8 is an exploded view of one embodiment of this apparatus for reversibly coupling the liquid cartridge 111 via a cartridge holder 128 coupled with the mechanical piston-moving device 120 showing the pneumatic bladder 126 contained in a bladder holder 127 and the holder 125 for the mechanical piston-moving device.

A second component is a means for providing a high acceleration to the rigid assembly. This is preferably achieved by momentum transfer caused by collision between the rigid assembly and another body which is initially moving relative to the rigid assembly. One embodiment is to strike the rigid assembly with a moving mass, thus generating acceleration to the rigid assembly by means, and of a magnitude, which may readily be calculated by those skilled in the art. However, as is known to those skilled in the art, deceleration is entirely equivalent to acceleration. Therefore, a preferred embodiment is to cause the rigid assembly to move into and to collide with a stationary mass, such as the base of the mechanical assembly.

A third component is a means for propelling the impacting mass in one embodiment, or the combined rigid assembly in the preferred embodiment, along a constrained path. The path may be constrained by a parallel swing arm linkage, a sliding bearing, or similar. The propelling mechanism may be active, such as a pneumatic or hydraulic cylinder, an electric motor, electromagnetic force, or passive such as a spring force or gravitation.

Figure 9:
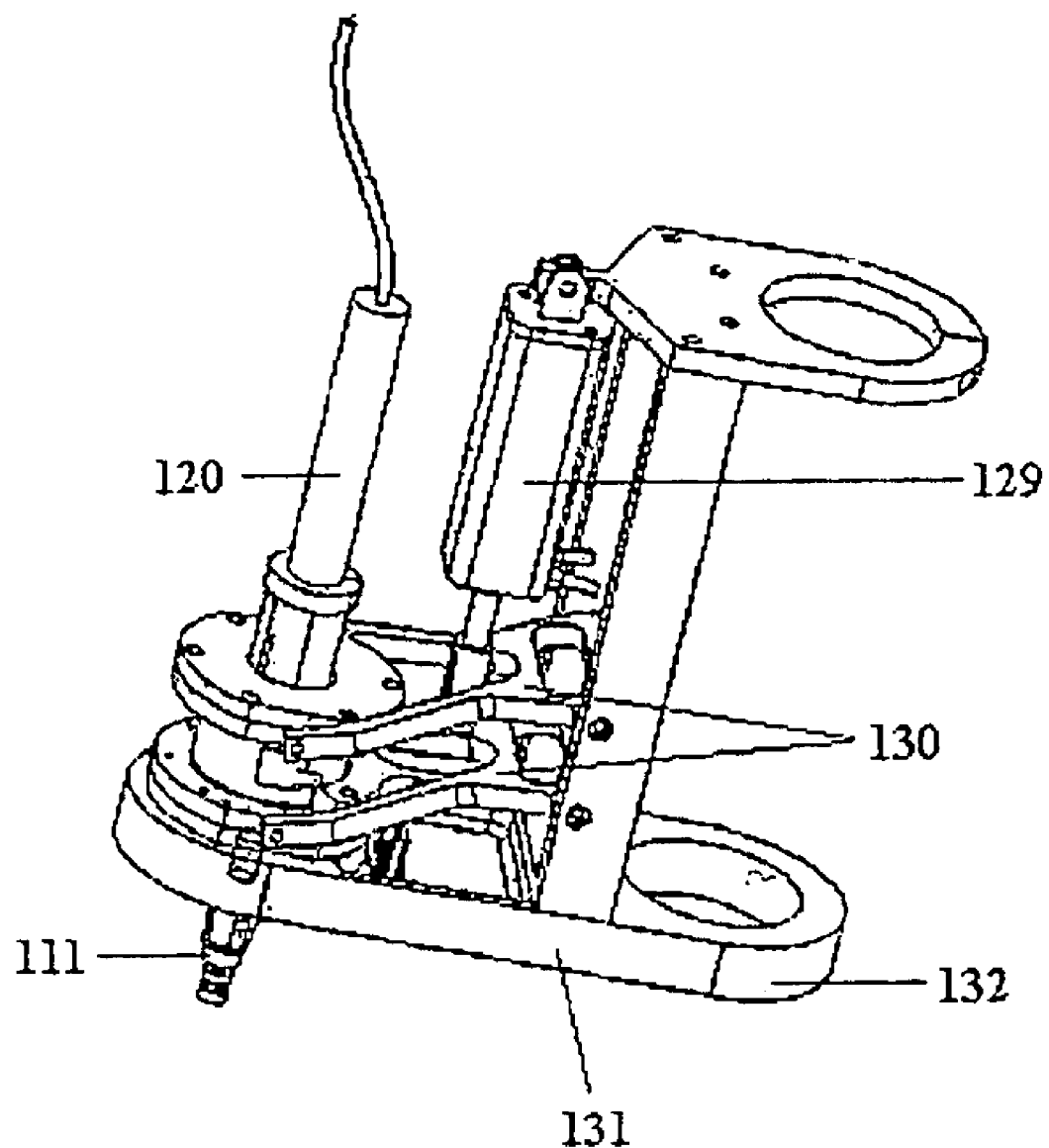
FIG. 9 is a perspective view of one embodiment of the apparatus for propelling the rigid liquid cartridge and piston-moving device into a stationary mass, thus imparting high deceleration to the liquid cartridge and detaching the microdrop.

FIG. 9 is a perspective view of one embodiment of the apparatus for propelling the pneumatic bladder coupled rigid liquid cartridge 111 and piston-moving device 120 held in two swing arms 130 which can be driven downward via a pneumatic piston 129 thus imparting high deceleration to the liquid cartridge upon striking a stationary mass 131, the base of the shown assembly, resulting in the detaching the microdrop from the dispensing tip.

Thus, improved precision dispensing of micro-drops is enabled without the disadvantages of the present art. Non-intrusive dispensing may be accomplished without the difficulty of detaching micro-drops, or requiring a "touch-off. The precision of the initial aliquot volume is maintained without the uncertainty involved in judging the "suck-back", or compliance relaxation of the container. The system and methods are readily adaptable to automated systems such as that disclosed in U.S. Pat. No. 6,387,330, incorporated by reference herein, thereby reducing human error and fatigue.

The objective of dispensing microliter aliquots in an accurate and precise manner is achieved by the present invention. The detection and position control of the liquid surface at the dispensing tip before the first aliquot is dispensed and reliably detaching the micro-drop from the dispensing tip after such any aliquot is dispensed are critical features for accurate and precise aliquot volume control enabled by the invention.

The invention permits the dispensing of precious liquids from the liquid cartridges in a manual, semi-automatic or fully automatic mode. In a semi-automatic or automatic mode the use of barcode labels or RFID tags on or in the liquid cartridges permit the automatic tracking and data reporting via a computer linked to the dispensing apparatus. In a fully automatic mode a robot is included into the system to transfer the liquid cartridges between holding trays for the cartridges and the dispensing unit. In the automatic mode the total history of the cartridge may be maintained including its age and the remaining quantity in the cartridge.

With respect to the above description, it is to be understood that the optimum dimensional relationships for the parts of the invention, to include variations in size, materials, shape, form, function, and manner of operation, assembly, and use, are deemed readily apparent to one skilled in the art, and all equivalent relationships to those illustrated in the drawings and described in the specification are intended to be encompassed by the present invention.

Therefore, the foregoing is considered to be illustrative only of the principles of the invention. Further, as numerous modifications and changes will readily occur to those skilled in the art, it is not desired to limit the invention to the exact construction shown and described, and accordingly, all suitable modifications and equivalents may be resorted to, falling within the scope of the invention.

What is claimed is:

1. A system for precision dispensing of liquids, comprising:
   a liquid cartridge having a substantially cylindrical body, a dispensing tip, and a sliding piston for driving a volume of liquid contained in the liquid cartridge through the dispensing tip;
   a piston-moving device for moving the sliding piston;
   a coupling device for reversibly coupling the liquid cartridge with the piston-moving device to form a rigid assembly;

a detecting device configured to accommodate the liquid cartridge and detect the presence of a liquid meniscus surface of a liquid drop on the dispensing tip of the liquid cartridge;

a detaching device configured to hold the rigid assembly and detach the liquid drop adhering to the dispensing tip by applying acceleration or deceleration to the rigid assembly; and a control device connected to the detecting device, the piston-moving device, and the detaching device, wherein the control device measures an apparent position change of the end of the dispensing tip caused by the detected presence of the liquid meniscus surface of the liquid drop, calculates a volume of the liquid drop based on the measured apparent position change, and controls the movement of the piston-moving device to dispense a required volume of liquid with proper compensation for the calculated volume of the liquid drop.

2. The system of claim 1, wherein the piston-moving device is a micrometer actuator controlled by the control device.

3. The system of claim 1, wherein the volume of the liquid cartridge is from 0.5 microliters to 10 milliliters.

4. The system of claim 1, wherein the detecting device comprises a diffuse light source to illuminate the dispensing tip, one or more lens to image the dispensing tip, and an electronic image detector.

5. The system of claim 1, wherein the detecting device comprises a point light source and an electronic image detector.

6. The system of claim 1, wherein the liquid cartridge is made of molded or machined plastic and comprises features on an outside of the body for engagement with the coupling device.

7. The system of claim 1, wherein the liquid cartridge has an attached or otherwise incorporated barcode label or RFID tag.

8. The system of claim 1, wherein the coupling device includes a cartridge holder coupled with the piston-moving device and a mechanism for engaging the cartridge holder with the liquid cartridge or releasing the liquid cartridge from the cartridge holder.

9. The system of claim 1, wherein the control device is a computer.

10. The system of claim 1, wherein the detaching device comprises a mechanism for holding and aligning the rigid assembly during a downward motion of the rigid assembly, and a stationary base upon which the rigid assembly strikes as a result of the downward motion of the rigid assembly whereby the liquid drop is detached and propelled from the dispensing tip into a receiver by a deceleration imparted to the rigid assembly.

11. A method for the precision dispensing of liquids using the system of claim 1, comprising:

providing the liquid cartridge having the substantially cylindrical body, the dispensing tip, and the sliding piston for driving a volume of liquid contained in the liquid cartridge through the dispensing tip;

reversibly coupling the liquid cartridge with the piston-moving device to form the rigid assembly;

moving the sliding piston by the piston-moving device for driving the volume of liquid contained in the liquid cartridge through the dispensing tip;

detecting the presence of a liquid meniscus surface of a liquid drop on the dispensing tip of the liquid cartridge with the detecting device accommodating the liquid cartridge;

detaching the liquid drop adhering to the dispensing tip by applying acceleration or deceleration to the rigid assembly with the detaching device holding the rigid assembly; and measuring with the control device an apparent position change of the end of the dispensing tip caused by the detected presence of the liquid meniscus surface of the liquid drop, calculating by the control device a volume of the liquid drop based on the measured apparent position change, and controlling by the control device the movement of the piston-moving device to dispense a required volume of liquid with proper compensation for the calculated volume of the liquid drop, wherein the control device is connected to the detecting device, the piston-moving device, and the detaching device.

* * * * *